US006277782B1

(12) United States Patent
Moller et al.

(10) Patent No.: US 6,277,782 B1
(45) Date of Patent: *Aug. 21, 2001

(54) CHIRAL ADSORBENTS AND PREPARATION THEREOF AS WELL AS COMPOUNDS ON WHICH THE ADSORBENTS ARE BASED AND PREPARATION OF THESE COMPOUNDS

(75) Inventors: Per Moller, Kungsbacka; Domingo Sanchez, Tollered; Stig Allenmark, Kullavik; Shalini Andersson, Linköping, all of (SE)

(73) Assignee: Eka Nobel AB, Bohus (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/448,430

(22) PCT Filed: Dec. 3, 1993

(86) PCT No.: PCT/SE93/01050

§ 371 Date: Jun. 26, 1995

§ 102(e) Date: Jun. 26, 1995

(87) PCT Pub. No.: WO94/12275

PCT Pub. Date: Jun. 9, 1994

(30) Foreign Application Priority Data

Dec. 3, 1992 (SE) .................................................... 9203646

(51) Int. Cl.⁷ .............................. B01J 20/22; B01J 20/26
(52) U.S. Cl. ......................... 502/402; 502/401; 502/407; 210/198.2; 210/656; 210/660
(58) Field of Search ................... 502/401, 402, 502/407; 210/198.2, 656, 660

(56) References Cited

U.S. PATENT DOCUMENTS

| | | | |
|---|---|---|---|
| 4,318,819 | * 3/1982 | Malloy et al. ......................... 252/184 |
| 4,882,048 | 11/1989 | Blaschke et al. .................. 210/198.2 |
| 4,914,159 | 4/1990 | Bömer et al. . | |
| 4,937,000 | * 6/1990 | Bomer et al. ......................... 210/656 |
| 5,096,971 | * 3/1992 | Nishikaji et al. .................... 525/278 |
| 5,162,155 | 11/1992 | Berndt et al. . | |
| 5,274,167 | * 12/1993 | Lange et al. ............................ 560/40 |
| 5,292,924 | 3/1994 | Grosser et al. . | |
| 5,347,042 | * 9/1994 | Grosse-Bley et al. ............... 560/153 |

FOREIGN PATENT DOCUMENTS

| | | | |
|---|---|---|---|
| 2045971 | 6/1991 | (CA) | ............................ C07C/233/09 |
| 263 711 A5 | 1/1989 | (DE) . | |
| 0 155 637 A2 | 9/1985 | (EP) . | |
| 0 249 078 | 7/1986 | (EP) | ............................... B01J/20/32 |
| 0 249 078 A2 | 12/1987 | (EP) . | |
| 0 270 095 A2 | 6/1988 | (EP) . | |
| 0 282 770 A1 | 9/1988 | (EP) . | |
| 0 464 487 | 3/1990 | (EP) | ............................. C07C/233/09 |
| 0 379 917 A2 | 8/1990 | (EP) . | |
| 0 417 586 A2 | 3/1991 | (EP) . | |
| 0 464 487 A1 | 1/1992 | (EP) . | |
| 0 464 488 A2 | 1/1992 | (EP) . | |
| 0 545 168 A1 | 6/1993 | (EP) . | |
| 60-193930A | 10/1985 | (JP) . | |
| 6277149 A | 12/1987 | (JP) . | |
| WO94/12275 | 3/1992 | (WO) . | |

OTHER PUBLICATIONS

J. Pharm. Biomed. Anal., vol. 2, No. 2, pp. 183–189, 1984.

J. Org. Chem., vol. 52, No. 12, pp. 2490–2496, 1987.

Ahuja, Satinder, *Chiral Separations by Liquid Chromatography,* 1991, pp. 114–125.*

Erlandson et al, "Direct Analytical and Preparative Resolution of Enantiomers Using Albumin Adsorbed to Silica as a Stationary Phase", J. of Chromatography, 370:475–483, 1986.

Doboshi et al., "A Chiral Stationary Phase Derived from (R,R)–Tartramide with Broadened Scope of Application to the Liquid...Enantiomers", J. Org. Ghem. 52:2490–2496, 1987.

Jürgen Falbe et al, Rompp Chemie Lexikon, 4167–4168, 1993.

Hans–George Elias, "Polymere Von Monomeren und Makromolekülen zu Werkstoffen", p. 361.

Saechtling, Kunststoff Taschenbuch, 25. Ausgabe, p. 60.

Bieleman, "Lackadditive", pp. 117–121, p. 130.

Merck, Reagenzien, Diagnostica Chemikalien, 1992/93, pp. 57–58, pp. 1340–1341.

* cited by examiner

Primary Examiner—Walter D. Griffin
Assistant Examiner—In Suk Bullock
(74) Attorney, Agent, or Firm—Burns, Doane, Swecker & Mathis, L.L.P.

(57) ABSTRACT

Optically active adsorbents based on network polymerized derivatives of dicarboxylic acids, diamines or diols which are chemically bonded to a carrier. The derivatives can be polymerized by radical polymerization or through hydrosilylation in the presence of a solid carrier. The optically active adsorbents are usable for chromatographic separation of racemic mixtures of enantiomers.

20 Claims, No Drawings

CHIRAL ADSORBENTS AND PREPARATION THEREOF AS WELL AS COMPOUNDS ON WHICH THE ADSORBENTS ARE BASED AND PREPARATION OF THESE COMPOUNDS

The present invention relates to new chiral adsorbents and to methods for preparing them. The invention also relates to certain new compounds on which the chiral adsorbents are based and to the preparation of these new compounds.

Optical isomers can be separated by the formation of diastereomers using chiral reagents, followed by separation using liquid or gas chromatography or crystallisation, or by direct chromatographic separation using chiral phase systems. The growing interest in resolving pharmaceutical substances and determining their enantiomeric purity has entailed an increased need of direct chromatographic separation OF ENANTIOMERS. This separation technique uses either a chiral selective substance in the mobile phase or a chiral stationary phase. In recent years, great attention has been paid to direct chromatographic separation of enantiomers using chiral stationary phases. A number of different chiral adsorbents have been suggested, but only a few of them, such as those based on cellulose derivatives or derivatised amino acids, have met with any appreciable commercial success in preparative chromatography. This largely depends on the stringent demands that are placed on chiral stationary phases to be suitable for preparative, i.e. large-scale, separations, primarily by HPLC (High Performance Liquid Chromatography). For such separations, the columns must have high enantioselectivity, high capacity, i.e. allowing the addition of relatively large amounts of racemate, high efficiency, i.e. giving small band broadening in the chromatogram, as well as high universality, i.e. allowing separation of as many structurally different types of chemical compounds as possible.

According to the present invention, chiral stationary phases based on network polymerised derivatives of dicarboxylic acids, diamines, dioles or hydroxy acids which are chemically bonded to a solid carrier have been found to thoroughly satisfy the demands placed on such phases for use in both analytical and preparative separations. One example of such an derivative is tartaric acid as such which is one of the less expensive optically active organic starting materials available on the market today, which makes the present invention in its different aspects economically attractive.

The optically active adsorbent according to the invention is characterized in an optically active network polymer covalently bound to a carrier.

The optically active network polymer comprises optically active derivatives of dicarboxylic acids, diamines, dioles or hydroxy acids.

Each functional group of the optically active derivatives of dicarboxylic acids, diamines or dioles comprises at least one aliphatic carbon residue with up to 15 carbon atoms and at least one terminal unsaturation.

Derivatives of diols are aliphatic esters, carbonates or carbamates having up to 15 carbon atoms in the carbon chain and a terminal unsaturation.

Derivatives of diamines are amides, carbamates and urea having up to 15 carbon atoms in the carbon chain and a terminal unsaturation.

Derivatives of the dicarboxylic acids are esters and amides having up to 15 carbon atoms in the carbon chain and a terminal unsaturation.

The most preferred derivative of the hydroxy acids is tartaric acid.

Examples of compounds of interest are:
D- or L-tartaric acid
(1R,2R)-(−)-1,2 diamino cyclohexan
(+)-2.2'-diamino binaphthyl -(1,1')
(1R,2R)-(−)-1,2-cyclohexan diol
(+)-(2R,3R)-1,45-dimethoxy-2,3-butandiol
D-(−)-citramalic acid
D-(+)-malic acid.

The invention is defined in more detail in the appended claims.

The adsorbents are according to one preferred embodiment of the present invention based on network polymerised tartaric acid derivatives which are bonded to a carrier, such as a silica gel ($SiO_2$ gel). As is known in the art, certain tartaric acid derivatives bonded to silica gel can be used as chiral stationary phases. Such phases with non-polymeric derivatives bonded to silica (so-called brush type) as well as a number of chiral applications for such tartaric acid derivatives, are described by W. Lindner and I. Hirschböck in J. Pharm. Biomed. Anal. 1984, 2, 2, 183–189. Chiral stationary phases based on a simple, non-polymeric tartaric acid derivative are also disclosed by Y. Dobashi and S. Hara in J. Org. Chem. 1987, 52, 2490–2496. The advantages of the tartaric acid derivative being part of a network polymer phase, as in the present invention, are that several chiral centres are obtained on the carrier, which results in increased capacity, and that a more protected carrier surface is obtained. For a silica carrier, this results in a reduced number of accessible free silanol groups, which means a decrease of achiral polar interactions, which impair the enantioselectivity. Enhanced enantioselectivity is also obtained with a polymer phase as compared with a monomer one, probably because the polymer can form a three-dimensional structure that can have chiral cavities.

The tartaric acid derivatives that are polymerised are in themselves optically homochiral derivatives and contain at least two stereogenic centres. The derivatives can be characterised by the general formula:

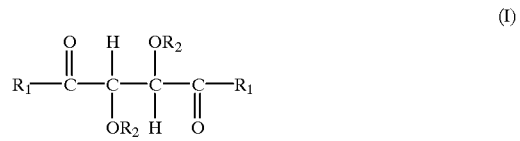

(I)

wherein $R_1$ is a group RNH—, RO—, RR'N— or HO— and $R_2$ is a group RNHCO—, RCO—, ROCO—, H— or R—, R being an aliphatic hydrocarbon residue having up to 15 carbon atoms, an aryl group, an aralkyl group, naphthyl group or an anthryl group and R' being hydrogen or an alkyl group having up to 7 carbon atoms, the derivatives containing at least two groups $R_1$ or $R_2$ containing an aliphatic unsaturation. $R_1$ and $R_2$ may contain one or more chiral centres. When R is an aliphatic hydrocarbon residue, this may be an alkyl, a cycloalkyl, an alkenyl or an alkynyl group. R then suitably contains up to 10 carbon atoms and suitably is an alkyl or alkenyl group and preferably an alkenyl group. R may be an aryl group or an aralkyl group. These groups may contain 1, 2 or 3 rings and be unsubstituted or substituted with one or more substituents on the ring or rings. Examples of such substituents are alkyl groups, hydroxy groups, halogens, nitro groups and alkenyl groups. R' suitably is hydrogen or an alkyl group having 1 or 2 carbon atoms. Suitably, $R_1$ is a group RNH—, RO— or RR'N—, and preferably a group RNH—. R then suitably is an allyl group, an alpha-phenylethyl group or a naphthyl group and most preferred any of the two first-mentioned ones. $R_2$ suitably is a group RNHCO—, RCO— or H— and preferably a group RNHCO— or RCO—. R then suitably is a phenyl, an allyl, a 3,5-dinitrophenyl, an naphthyl, a methacryl, an alpha-phenylethyl, a 3,5-dimethylphenyl, a tertiary-butyl, or an isopropyl group. Preferably, R is a phenyl, an allyl, a 3,5-dinitrophenyl, an naphthyl, a methacryl or an alpha-phenylethyl group. The two groups $R_1$ in the derivatives should be equal, and the two groups $R_2$ should also be equal.

Especially suitable are tartaric acid derivatives of formula I which can be characterised by the formulae

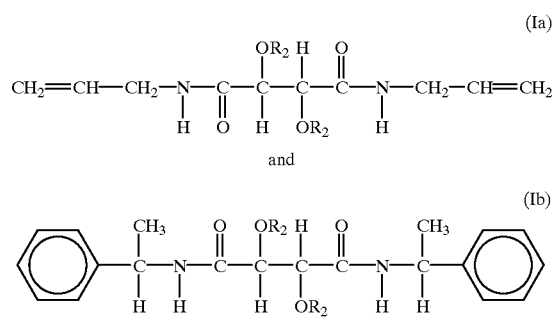

In compounds of formula Ia, $R_1$ thus is an allyl amine residue, and in compounds of formula Ib, $R_1$ is a phenylethyl amine residue and $R_2$ is as defined above.

Compounds of formula Ia include diallyl tartaric diamide (R,R or S,S) which is commercially available, and derivatives thereof. In compounds of formula Ia, $R_2$ suitably is a group RNHCO—, RCO— or H, R being as defined above. R may, for example, be a bulky alkyl group, such as isopropyl or tertiary butyl, a benzyl group, a phenyl group, a naphthyl group or an anthryl group, and any substituents on the aromatic ring may be any of those indicated above. Most preferred, $R_2$ is a group RNHCO— or RCO—, where R contains an aryl group, which optionally is substituted. Advantageously, the compounds contain an aromatic nucleus, since π,π-interactions are then obtained with aromatic racemates, which may confer advantages in separation. Examples of some specific, suitable groups $R_2$ for compounds of formula Ia are: phenyl carbamoyl, α-phenylethyl carbamoyl, 3,5-dimethylphenyl carbamoyl, naphthyl carbamoyl, α-naphthylethyl carbamoyl, benzoyl, and 3,5-dinitrobenzoyl, and 3,5-dimethylbenzoyl.

Compounds of formula Ia can be prepared by conventional acylation and carbamoylation reactions. Esters of diallyl tartaric diamide can thus be prepared by reacting the diamide with the corresponding acid chloride or acid anhydride. Suitably, the diamide is dissolved in a solvent which also acts as a base, e.g. pyridine, whereupon the corresponding acid chloride is added, suitably in an at least equimolar amount. After completion of the reaction, which may be conducted at room temperature, the resulting product is processed in conventional manner, such as by extraction, evaporation and crystallisation. Carbamates of the diallyl tartaric diamide can be prepared by reacting the amide with the corresponding isocyanate. The amide can be dissolved in a suitable solvent, such as tetrahydrofuran, and be reacted with the isocyanate in the presence of a catalytic amount of base, e.g. 4-dimethylaminopyridine, or a catalyst, e.g. a tin salt. The reaction is suitably conducted by refluxing, and after completion of the reaction, the product is isolated by conventional processing.

Compounds of formula Ib can be prepared from the reaction product of an ester of R,R— or S,S— tartaric acid, such as alkyl tartrate, e.g. dimethyl tartrate, and an optically active α-phenylethyl amine. $R_2$ in compounds of formula Ib suitably is a group RNHCO— or RCO— and then R must thus contain an aliphatic double bond, preferably a terminal one. Especially suitable groups $R_2$ are

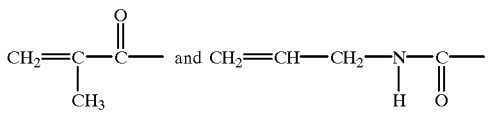

Compounds having such groups $R_2$ can be prepared by known acylation reactions from anhydride and known carbamoylation reactions, respectively. For the preparation of compounds according to formula Ib, where $R_2$ is a methacrylic acid residue, the diamide is reacted with methacrylic acid anhydride. The diamide can be solved in a suitable solvent, such as tetrahydrofuran or chlorinated hydrocarbon, and be reacted with the diamide in the presence of a base, such as 4-dimethylaminopyridine at room temperature. For preparing compounds of formula Ib which are carbamates, the same procedure as used for preparing carbamates of formula Ia can be adopted.

The polymerised derivatives are covalently bonded to the carrier material, and the network polymerisate itself can be homo- or copolymers of the indicated tartaric acid derivatives or such polymers that have been prepared by hydrosilylation reactions.

The carrier may be an organic or inorganic material. Examples of organic carriers are styrene-divinyl benzene polymers. Examples of inorganic carriers are silica, aluminum oxide and zirconium oxide which are modified with silanes. The polymerised derivatives are bonded to organic carriers by a C—C bond and to inorganic carriers by an Si—C or Si—O—Si bond. The carrier materials should have a high specific surface and satisfactory mechanical stability. The surface of the carrier material should contain a reactive functional group which either contains a terminal double bond, hydrosilyl group or the silanol group, so that the tartaric acid derivatives can be bonded to the carrier. Examples of suitable groups containing a double bond are vinyl, hexenyl, octenyl, acrylic and methacrylic groups. Such groups, as well as hydrosilyl groups, can be bonded to the surface of the carrier material as silica by known surface-modifying reactions. Structurally, some different, suitable hydrosilyl-modified silica surfaces can be schematically defined as follows:

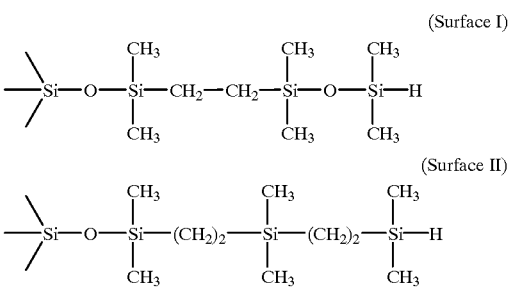

(Surface III)

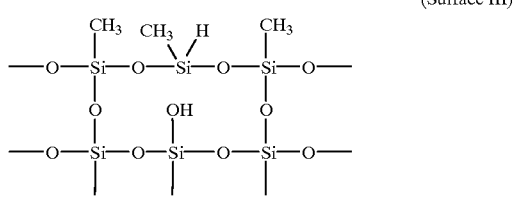

Surfaces I and II have been prepared by modifying a vinyl surface with 1,1,3,3-tetramethyldisiloxane and 1,1,4,4-tetramethyldisilylethylene, respectively. Surface III has been prepared by modifying non-derivatised silica with 1,3,5,7-tetramethylcyclotetrasiloxane. A variant of surface III can be prepared by using 1,3,5,7-tetravinyl tetramethylcyclotetrasiloxane and, by polymerisation thereof, modifying the silica surface, which is advantageous to provide optimal coverage of the surface.

The optically active adsorbents according to the present invention can be prepared by network polymerising the tartaric acid derivatives in the presence of carrier material or by first polymerising the derivatives and then anchoring the network polymer to the carrier material by covalent bonding.

For certain purposes it might also be suitable to use the tartaric acid derivatives according to formula I as monomers for producing linear tartaric acid polymers. In such cases polymerisation of a tartaric acid derivative containing two terminal unsaturated groups are polymerised either by radical polymerisation or by using a bifunctional hydrosilane or hydrosiloxane.

Network polymerisation of the tartaric acid derivatives, which may exist in R,R-form or S,S-form, can be performed by radical polymerisation or by a hydrosilylation polymerisation reaction. The original chirality of the derivatives is maintained in the polymerisation. Radical polymerisation can be performed by conventional technique. Use is then made of free-radical forming initiators such as azo compounds and peroxides, elevated temperatures of from about 50 to 150° C. and reaction times of from about 1 to 24 hours. The polymerisation is conducted in an organic solvent, such as toluene, chloroform or dioxan.

Polymerisation through, hydrosilylation is performed using hydrosilanes or hydrosiloxans. Suitable hydrosilanes and hydrosiloxanes can be defined by the general formula

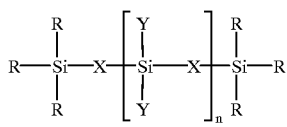

wherein R is an alkyl group having 1–4 carbon atoms or H or A mixture thereof, X is $(CH_2)_M$ or O and Y is R or the group

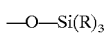

and n is an integer from 0 to 3000, M is an integer from 0 to 10. Polymerisation through hydrosilylation is known per se and described, e.g., in J. Chromatogr. 1992, 594, 283–290. The basic technique disclosed therein can be used for preparing the present chiral adsorbents. The reaction is suitably performed by using a metal complex as catalyst, for example a complex of platinum or rhodium, at temperatures of from about 50 to 180° C., most preferred above 100° C.

Solvents that are inert to hydrosilylation are used as polymerisation medium. Examples of such solvents are toluene, dioxan, mixtures of toluene and dioxan, chloroform, tetrahydrofuran and xylene. Since polymerisation through hydrosilylation is a relatively slow reaction, periods of time from 1 up to about 48 hours may be required.

Radical polymeration is performed in the presence of carrier material and is most effective when the carrier materials have a surface of the above-mentioned styryl, methacryloyl, methacrylamide or acrylamide type and also the tartaric acid derivatives contain these groups. Network polymerisation through hydrosilylation is however preferable. Such polymerisation shows excellent effectiveness with all of the above-mentioned types of surfaces. The hydrosilanes will not only be included to a varying extent as comonomers in polymerisates of tartaric acid derivatives but also provide bonding to the carrier material. Network polymerisation through hydrosilylation can be performed in the presence of carrier material or in the absence thereof. In the latter case, anchorage to the carrier surface is performed by BRINGING the carrier and the polymer in contact with each other, suitably by adding the carrier material directly to the solution of the polymer. Free hydrosilyl groups on the network polymer then bind to the modified carrier surface in the presence of catalyst and at the elevated temperatures used in polymerisation.

Suitably, use is made of from 1 to 30 μmol of monomeric tartaric acid derivative per m² of carrier surface and of from 1 to 30 μmol of hydrosilane per m² of carrier surface. Such a high degree of coverage, in μmol per m² of silica, is of course desirable, and the present method can yield satisfactory degrees of coverage of at least about 0.70 μmol/m².

The present invention also relates to an optically active adsorbent which is prepared by network polymerisation through hydrosilylation of tartaric acid derivatives of formula I in the presence of a hydrosilane or a hydrosiloxane and a carrier material which is surface-modified so that the surface has one terminal double bond or is a hydrosilyl group, and relates also to an adsorbent prepared by network polymerisation through hydrosilylation of tartaric acid derivatives of formula (I) in the presence of a hydrosilane or a hydrosiloxan, whereupon the carrier material, which is surface-modified so that the surface has one reactive functional group which either contains a terminal double bond or is a hydrosilyl group, is added to the resulting polymer solution.

The products prepared as above, i.e. the carrier materials coated with polymerisate, are filtered off and washed with solvent, and are dried. Drying can be conducted at 80–90° C. and suitably under vacuum. The thus prepared chiral adsorbents can thereafter be packed under pressure in chromatography columns in known manner.

The chiral adsorbents according to the present invention have, when used chromatographically, excellent properties in respect of universality, enantioselectivity and capacity. They can be used for direct enantiomeric separation and are well suited for use in HPLC. The chiral adsorbents can be used for both analytical and preparative purposes and for separation of a very large number of racemates of varying chemical consistution, with very good selectivity. Examples of different types of racemic pharmaceutical substances that can be separated using the present chiral adsorbents are benzodiazepinones, benzothiadiazines, dihydropyridines and lactams.

Some of the tartaric acid derivatives used for preparing the chiral adsorbents are new compounds, and the invention also comprises such new compounds which can be characterised by the formula:

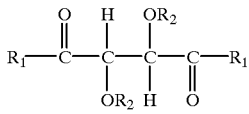
(II)

wherein $R_1$ is a group RNH—, RO—, RR'N— or HO— and $R_2$ is a group RNHCO—, RCO—, ROCO—, H— or R—, R being an aliphatic hydrocarbon residue having up to 15 carbon atoms, an aryl group or an aralkyl group or a polyaromatic group and R' being hydrogen or an alkyl group having up to 7 carbon atoms, the derivatives containing at least two groups $R_1$, or $R_2$ containing an aliphatic unsaturation, $R_1$, being however not a phenylethyl amino residue when $R_2$ is H. For the groups $R_1$, and $R_2$, R and R', suitable and preferred groups correspond to what has earlier been stated for the derivatives of formula I.

Especially preferred compounds are such having the formulae

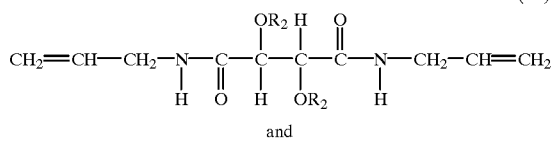
(IIa)

and

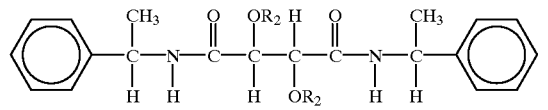
(IIb)

wherein $R_2$ is a group RNHCO—, RCO— or R—, where R is as defined above. For compounds of formula IIb, R is however an aliphatic hydrocarbon residue having up to 15 carbon atoms and containing a double bond. Suitable and preferred compounds otherwise correspond to what has earlier been stated for the derivatives of formulae Ia and Ib.

The new compounds can be prepared according to the general methods which have been described above and which will be described in more detail hereinafter.

The invention will be described more thoroughly in the following non-restricting Examples. Figures in parts and per cent are parts by weight and per cent by weight, respectively, unless otherwise stated.

EXAMPLE 1

This Example shows the preparation of chiral tartaric acid derivatives.

1a) Preparation of (+)-N,N'-bis-(α-phenylethyl)-L-tartaric diamide (+)-Dimethyl-L-tartrate (20.0 g, 0.112 mol) was dissolved in methanol (200 ml), whereupon D(+)-α-phenylethyl amine (135 ml, 1.058 mol) was added. The solution was subjected to refluxing for 3 days. The methanol solution was evaporated to dryness under vacuum. The residue was dissolved in methylene chloride (2 l). The methylene chloride phase was extracted with HCl (10%, 3×400 ml), NaHCO$_3$ solution (5%, 2×200 ml) and water (1×200 ml). The methylene chloride phase was dried with Na$_2$SO$_4$ (anhydrous), whereupon the solution was evaporated to dryness under vacuum. The residue was recrystallised in acetonitrile twice (2×200 ml), whereupon white crystals were obtained (20.9 g, yield: 52%).

The product was analysed and the following results were obtained: Purity according to HPLC (220 nm):>99%. Melting point: 131–132° C. $[\alpha]_D^{25}$: +16.0° (MeOH, c=1.05). H'NMR (60 MHz, DMSO-D$_6$:δ:1.40 (d,6H), 4.27 (d,2H), 4.99 (m,2H), 5.64 (d,2H), 7.31 (m,10H), 7.92 (d,2H).

1b) Preparation of O,O'-dimethacryloyl-(+)-N,N'-bis-(α-phenylethyl-L-tartaric diamide (+)-N,N'-bis-(α-phenylethyl)-L-tartaric diamide (14.0 g, 39.3 mmol) was dissolved in dioxan (280 ml) at room temperature. Methacrylic anhydride (12.9 ml, 86.5 mmol) and 4-dimethylaminopyridine (10.6 g, 86.5 mmol) were then added. The solution was left with stirring at room temperature for 4 h. The dioxan solution was evaporated to dryness at 30° C. under vacuum. The residue was dissolved in methylene chloride (350 ml). The methylene chloride phase was extracted with HCl (10%, 3×200 ml), NaHCO$_3$ solution (1×200 ml, 5%) and water (1×200 ml). The methylene chloride phase was dried with Na$_2$SO$_4$ (anhydrous), and thereafter evaporated to dryness at 30° C. under vacuum. 20.9 g of product was obtained as an oil. This oil was purified by preparative liquid chromatography: Column: 5×25 cm with Kromasil®-C18, 16 μm. After this purification, a white crystalline product (11.5 g, yield: 60%) was obtained.

The product was analysed and the following results were obtained: Purity according to HPLC (220 nm):>99%. Melting point: 129–130° C. $[\alpha]_D^{25}$: +60.4 g (MeOH, c=1.0). H'NMR (60 MHz, CDCl$_3$):δ:1.43 (d,6H), 1.92 (S,6H), 5.06 (m,2H), 5.70 (m,4H), 6.16 (S,2H), 6.51 (6m,2H), 7.24 (m,10H).

1c) Preparation of O,O'-di-(allyl carbamoyl)-(+)-N,N'-bis-(αphenylethyl)-L-tartaric diamide (+)-N,N'-bis-(α-phenylethyl)-L-tartaric diamide (10.0 g, 28.0 mmol) was dissolved in tetrahydrofuran (300 ml). 4-dimethylaminopyridine (7.9 g, 64.6 mmol) and allyl isocyanate (11.4 ml, 129 mmol) were then added. The solution was subjected to refluxing with stirring for 24 h. The product which precipitated in tetrahydrofuran after 24 h was filtered and washed with tetrahydrofuran and petroleum ether (boiling point 30–40° C.). 12.9 g of white crystalline product was obtained. The product was recrystallised in dimethyl formamide (30 ml), filtered and washed with tetrahydrofuran. After recrystallisation, 11.0 g of product (yield: 75%) was obtained.

The product was analysed and the following results were obtained: Purity according to HPLC (220 nm):>99%. Melting point: 225° C. $[\alpha]_D^{25}$: +7.6° (DMSO, c=1.02). H'NMR (400 MHz, DMSO-D$_6$):δ:1.38 (d,6H), 3.61 (m,4H), 4.93 (m,2H), 5.04 (d,2H), 5.13 (d,2H), 5.51 (s,2H), 5.75 (m,2H), 7.23 (m,10H), 7.37 (t,2H), 8.03 (d,2H).

1d) Preparation of O,O'-di-(3,5-dinitrobenzoyl)-N,N'-diallyl-L-tartaric diamide

N,N'-diallyl-L-tartaric diamide (14.6 g, 63.95 mmol) was dissolved in pyridine (50 ml). 3,5-Dinitrobenzoyl chloride (30.18 g, 130.9 mmol) was then added with ice cooling. The solution was left with stirring for 3 h at room temperature.

The pyridine solution was supplied with methylene chloride (1.0 l), whereupon the methylene chloride phase was extracted with HCL (10%, 3×300 ml), NaHCO$_3$ (5%, 2×200 ml) and water (1×200 ml). The methylene chloride phase was dried with Na$_2$SO$_4$ and evaporated to dryness. A yellow-white crystalline residue was obtained. The residue was recrystallised in dimethyl formamide (70 ml), and a white crystalline product was obtained (32.0 g, yield: 81%).

The product was analysed and the following results were obtained: Purity according to HPLC (220 nm):>99%. Melting point: 232–233° C. $[\alpha]_D^{25}$: −75° (DMSO, c=1.02). H'NMR (60 MHz, $^-$DMSO-D$_6$):δ:3.71 (m,4H), 4.94 (m,4H), 5.65 (m,2H), 5.99 (S,2H), 8.85 (d,2H), 9.0 (m,6H).

1e) Preparation of O,O'-di((R)-α-phenylethyl)-carbamoyl-N,N'-diallyl-L-tartaric diamide N,N'-diallyl-L-tartaric diamide (4.6 g, 20 mmol) was dissolved in dry tetrahydrofuran (100 ml) with stirring. 4 drops of triethylamine were then added and (+)-phenylethyl isocyanate (6.8 ml, 48 mmol) was added dropwise. When the total amount of the isocyanate had been added, the reaction mixture was subjected to refluxing for 36 h. The reaction solution was evaporated and the residue was dissolved in methylene chloride and extracted with diluted H$_2$SO$_4$, NaHCO$_3$ solution and H$_2$O. The organic phase was dried with MgSO$_4$, evaporated and the residue was recrystallised from a dimethyl formamide/methanol mixture. White needles were obtained, and the yield was 54%.

The product was analysed and the following results were obtained: Melting point: 268.6–269.7° C. $[\alpha]_D^{25}$: +20° (DMSO, c=1) H'NMR (400 MHz, DMSO-D$_6$):δ:1.36 (d,6H), 3.64 (m,4H), 4.62 (m,2H), 4.92 (d,2H), 5.05 (d,2H), 5.34 (S,2H), 5.68 (m,2H), 7.29 (m,10H), 7.69 (d,2H), 7.94 (m,2H).

1f) Preparation of O,O'-dibenzoyl-N,N'-diallyl-L-tartaric diamide

N,N'-diallyl-L-tartaric diamide (1 g) was dissolved in pyridine (4 ml), and the solution was left with stirring at about 5° C. Benzoyl chloride (1.26 g) was added dropwise. The reaction mixture was thereafter left with stirring for about 1 h at room temperature, whereupon methylene chloride (50 ml) was added. The organic phase was extracted with 1 M H$_2$SO$_4$, water, saturated NaHCO$_3$ solution and water. The organic phase was dried over Na$_2$SO$_4$. Methylene chloride was evaporated and the residue was recrystallised from a mixture of acetone and hexane.

The product was analysed and the following results were obtained: Melting point: 200–201° C. $[\alpha]_D^{20}$: −120°±2° (c=0.5 in acetone) H'NMR (60 MHz, DMSO-D$_6$):δ:3.68 (4H,m), 4.92 (4H,m), 5.58 (2H,m), 5.84 (2H,s), 7.64 (6H,m), 8.08 (4H,m), 8.64 (2H,t).

1 g) Preparation of O,O'-diphenylcarbamoyl-N,N'-diallyl-L-tartaric diamide

N,N'-diallyl-L-tartaric diamide (4.6 g, 20 mmol) was suspended in 150 ml of dry CHCl$_3$. 4 drops of triethyl amine were added with stirring. The mixture was subjected to refluxing until the diamide had been dissolved. Phenylisocyanate (5.2 ml, 48 mmol) was thereafter added dropwise to the mixture. The reaction mixture was subjected to refluxing with stirring for 12 h. The cooled solution was extracted with 50 ml 1M H$_2$SO$_4$, 50 ml saturated NaHCO$_3$ solution and 2×50 ml H$_2$O. The organic phase was dried with MgSO$_4$, evaporated and the residue was recrystallised from a mixture of tetrahydrofuran and methanol. White needles were obtained, and the yield was 82%.

The product was analysed and the following results were obtained: Melting point: 253.2–255° C., $[\alpha]_D^{20}$: −83.4°, (c=0.5 in DMSO). $[\alpha]_D^{20}$: −60.8° (c=1.0 in THF). H'NMR (60 MHz, DMSO-D$_6$) δ:3.72 (4H,m), 5.04 (4H,m), 5.62 (2H,s), 5.76 (2H,m), 6.92 (2H,m), 7.00 (2H,m), 7.28 (4H, m), 7.46 (4H,m), 8.30 (2H,t).

1h) Preparation of O,O'-dinaphthylcarbamoyl-N,N'-diallyl-L-tartaric diamide

N,N'-diallyl-L-tartaric diamide (0.46 g, 2 mmol) was dissolved in 200 ml of dry tetrahydrofuran. 1 drop of triethyl amine was added. 1-Naphthyl isocyanate (0.69 ml, 4.8 mmol) was thereafter added dropwise. The reaction mixture was subjected to refluxing for 36 h. A thick red-white precipitation was obtained and filtered off, washed with 50 ml of methanol and recrystallised from a mixture of dimethyl formamide and methanol. White needles were obtained, and the yield was 33%.

The product was analysed and the following results were obtained: $[\alpha]_D^{25}$: −24° (DMSO, c=1). H'NMR (400 MHz, DMSO-D$_6$):δ:3.82 (m,4H), 5.03 (d,2H), 5.21 (d,2H), 5.65 (s,2H), 5.82 (m,2H), 7.54 (m,8H), 7.77 (m,2H), 7.92 (m,2H), 8.07 (m,2H), 8.36 (t,2H), 9.63 (m,2H),

EXAMPLE 2

This Example illustrates surface modification of an original carrier material for introduction of functional groups.

I. Surface modification for introducing a functional group containing a terminal double bond 10 g of Kromasil®, a silica material produced by Eka Nobel AB, Sweden and having an average particle size of 5 μm, an area of 256 m$^2$/g and an average pore diameter of 150 Å, was slurried in 50 ml of methylene chloride. Monochlorosilane (8 μmol/m$^2$ SiO$_2$) and pyridine (8 μmol/m$^2$) were then added. The solution was subjected to refluxing in a nitrogen atmosphere with stirring for 24 h. The solution was thereafter filtered and the derivatised silica was washed with methylene chloride, tetrahydrofuran and methanol. The surface-modified silica material was then dried at 80–90° C. for 24 h. The following different monochlorosilanes were used for surface modification as above:

Dimethylvinyl chlorosilane
Trivinyl chlorosilane
m,p-styrylethyldimethyl chlorosilane
6-hex-1-enyldimethyl chlorosilane
7-oct-1-enyldimethyl chlorosilane
3-methacryloxy propyldimethyl chlorosilane Another method for introducing of vinyl groups on the surface was also used. A vinyl-containing cyclic tetrasiloxane was used for modifying the same silica material as above. The silica material (10 g) was slurried in 50 ml of toluene. Tetravinyl tetramethyl-cyclotetrasiloxane (8.0 μmol/m$^2$ SiO$_2$) and trifluoromethane sulphonic acid (10 mg, catalytic amount) were then added. The solution was subjected to refluxing under nitrogen atmosphere with stirring for 18 h. The solution was thereafter filtered and the derivatised silica was washed with methylene chloride, tetrahydrofuran and methanol. The surface-modified silica material, with polymeric vinyl surface, was thereafter dried at 80–90° C. for 24 h.

II. Surface modification for introducing a hydrosilyl group

IIa) 5 g of the silica material Kromasil®, which had been surface-modified with vinyldimethyl chlorosilane, was suspended in 25 ml of chloroform, whereupon an $H_2PtCl_6$ solution (0.15 ml, concentration: 55 mg/ml isopropanol) was added. 1,1,3,3-tetramethyldisiloxane (8.0 $\mu$mol/m$^2$ SiO$_2$) was thereafter added. The solution was subjected to refluxing in nitrogen atmosphere for 18 h. The derivatised silica was washed and thereafter dried as earlier. This method yielded a coverage degree with respect to hydrosilane of 1.72 $\mu$mol/m$^2$ SiO$_2$. $\delta$C:2.0%.

IIb) Surface modification was performed in the same way as according to IIa, but with the difference that toluene was used instead of chloroform and the silane reagent was 1,1,4,4-tetramethyldisilyl ethylene. The coverage degree with respect to hydrosilane was 1.64 $\mu$mol and $\delta$C:2.35%.

IIc) In this mode of execution, the base material was non-modified Kromasil®. 5.0 g of the silica material was slurried in 25 ml of toluene. 1,3,5,7-Tetramethyl cyclotetrasiloxane (8.0 $\mu$mol/m$^2$ SiO$_2$=2.50 ml) and trifluoromethane sulphonic acid (10 mg) were then added. The solution was subjected to refluxing in nitrogen atmosphere for 18 h. The coverage degree was 8.80 $\mu$mol/m$^2$ SiO$_2$, $\delta$C:2.35%.

EXAMPLE 3

The following Example illustrates polymerisation, by hydrosilylation polymerisation, of tartaric acid derivatives on silica carriers. The silica material used was Kromasil® in all cases.

a) 5.0 g of silica material, modified with vinyl, was suspended in 30 ml of a 1:1 mixture of toluene and dioxan, whereupon an $H_2PtCl_6$ solution (0.10 ml, concentration: 60 mg/ml isopropanol) was added. Polymethylhydrosiloxan (Mw 360–420, 2.8 ml) was thereafter added. The solution was subjected to refluxing under nitrogen atmosphere for 2 h. O,O'-dibenzoyl-N,N'-diallyl-L-tartaric diamide (10 mmol) was thereafter ADDED. The solution was subjected to refluxing for another 18 h in nitrogen atmosphere. The thus treated silica material was filtered off and washed with dioxan, acetonitrile and tetrahydrofuran. The material was thereafter dried at 90° C. under vacuum for 24 h.

An elementary analysis gave in per cent by weight: C:16.15% ($\delta$C:11.5%), N:0.38% (0.56 $\mu$mol/m$^2$ (with respect to dibenzoyl diallyl tartaric diamide).

b) O,O'-(1-naphtoyl) -N,N'-diallyl-L-tartaric diamide (8.9 mmol, 4.79 g) was dissolved in toluene:dioxane (1:1, 45 ml) whereupon an $H_2PtCl_6$ solution (0.15 ml, concentration: 55 mg/ml isopropanol) as well as tertrakis (dimethyl siloxy) SILANE (6.7 mmol, 2.50 ml) was added. The solution was subjected to refluxing in nitrogen atmosphere for 24 h. Thereafter 5.0 G of carrier material (Kromasil®, modified with vinyl was added to the solution. The reaction was left further 24 hours with reflux under nitrogen. The product was filtered and washed with tetrahydrofurane, toluene and dichloromethane and dried at 90° C. under vacuum for 24 h. An anaylsis of carbon and nitrogen content gave gave 9.1 and 0.30 respectively, in per cent by weight, which corresponds to 0.44 $\mu$molm2 SiO$_2$.

c) 5.0 g of carrier material (Kromasil®, modified with vinyl), was suspended in 45 ml of tetrahydrofuran. $H_2PtCl_6$ (0.15 ml, concentration: 55 mg/ml isopropanoi), tertrakis (dimethyl siloxy) silane (7.5 mmol, 2.8 ml) and O,O'-diphenylcarbamoyl-N,N'-diallyl-L-tartaric diamide (10.25 $\mu$mol, 4.8 g) were thereafter added. The solution was placed in an autoclave. The reaction was left at 125° C. during 18 hours under nitrogen atmosphere. The product was filtered off and washed with dimethylformamide and tetrahydrofuran. An anaylsis of carbon and nitrogen content gave 12.1 and 0.95 respectively, in per cent by weight, which corresponds to 0.72 $\mu$mol/m$^2$ SiO$_2$.

d) O,O'-dibenzoyl-N,N'-diallyl-L-tartaric diamide (10.0 mmol, 4.36 g) was dissolved in toluene:dioxan (1:1, 30 ml), whereupon a solution of $H_2PtCl_6$ (0.15 ml, concentration: 55 mg/ml isopropanol) was added. Tetrakis(dimethyl siloxy) silane (7.5 mmol, 2.8 ml) was thereafter added. The solution was subjected to refluxing in nitrogen atmosphere for 24 h. 5.0 g of carrier material (Kromasil® modified with vinyl) was thereafter added to the solution. The reaction was allowed to proceed for another 24 h with refluxing in nitrogen atmosphere. The product was filtered and washed with tetrahydrofuran, toluene and dichloromethane and dried for 24 h at 90° C. under vacuum. An analysis of the carbon content and the nitrogen content showed 11.85% by weight and 0.50% by weight, respectively, corresponding to 0.76 $\mu$mol/m$^2$ SiO$_2$.

EXAMPLE 4

This Example illustrates chromatography using a chiral stationary phase according to the invention.

Silica material with network polymerised tartaric acid derivative according to Example 3D) was packed with conventional slurry-packing technique in a stainless steel HPLC column (4.6×250 mm). Enantioselectivity for a number of test racemates was examined. The test racemates were pharmaceutical preparations which are indicated in the following Table under their registered trademarks and with an indication of structural type or chemical or generic name. The enantioselectivity is expressed as $\alpha$, which is a measure of the ratio between the capacity factors of the enantiomers. $k'_1=(t_1-t_0)/t_0$; $k'_2=(t_2-t_0)/t_0$; $\alpha=k'_2/k'_1$ wherein $t_1$, and $t_2$=retention times for enantiomers as first and as last eluted, respectively, $t_0$=retention time for unretarded compound, $k'_1$ and $k'_2$ =capacity factors for enantiomers as first and as last eluted, respectively.

| Test racemate | Structural type | $\alpha$ | $k'_1$ | Mobile phase |
|---|---|---|---|---|
| Oxazepam | Benzodiaz- | 1.13 | 3.71 | A |
| Lopirazepam | epinones | 1.59 | 4.73 | A |
| Bendroflumethiazide | Benzothia- | 1.22 | 7.3 | A |
| Paraflutizide | diazines | 1.19 | 12.68 | A |
| Felodipine | Dihydro- | 1.0 | 3.71 | B |
| 152/80* | pyridines | 1.09 | 5.80 | A |
| Ibuprofen | Profens | 1.32 | 2.27 | F |
| Ketoprofen | | 1.12 | 5.38 | F |
| Baclofenlactam | Lactam | 1.13 | 2.82 | B |
| Hexobarbital | Barbiturate | 1.04 | 2.98 | E |
| Chlormezanone | | 1.13 | 6.39 | B |
| Chlorthalidone | | 1.50 | 3.83 | B |
| Warfarin | | 1.13 | 5.13 | D |
| 1,1'-Bi(2-naphthol) | | 1.26 | 2.29 | B |
| 1-(9-Anthryl)-2,2,2-trifluoroethanol | | 1.10 | 4.06 | C |
| 1-Phenylethanol | | 1.08 | 0.86 | C |
| Benzylmandelate | | 1.16 | 1.21 | I |
| 1-(9-fluorenyl)ethanol | | 1.05 | 2.32 | I |
| Metoprolo | $\beta$-amino | 1.08 | 2.78 | G |
| Propranolol | alcohols | 1.03 | 6.68 | H |
| Clenbuterol | | 1.32 | 0.57 | K |

The mobile phases indicated by letters were:
A=hexane:isopropanol (90/10)
B=hexane:isopropanol (95/5)
C=hexane:isopropanol (98/2)
D=hexane:isopropanol (99/1)
E=hexane:dioxan (95/5)

F=hexane:isopropyl alcohol:trifluoroacetic acid (99.4/0.5/0.1)
G=hexane:isopropyl alcohol:trifluoroacetic acid (94.9/5/0.1)
H=hexane:isopropyl alcohol:trifluoroacetic acid (96.9/3/0.1)
I=hexane:isopropyl alcohol (99.5/0.5)
K=methylene chloride:ethanol:trifluoroacetic acid (97.9/2/0.1)

The indicated mixing ratios are in per cent by volume.

As appears from the results indicated in the Table, these chiral stationary phases which are based on network polymers of tartaric acid derivatives exhibit a general enantioselectivity for most types of pharmaceutical substances.

We claim:

1. An optically active adsorbent comprising an optically active network polymer covalently bonded to a carrier.

2. The optically active adsorbent according to claim 1, wherein the optically active network polymer comprises optically active derivatives of dicarboxylic acids, diamines, diols or hydroxy acids.

3. The optically active adsorbent according to claim 2, wherein each functional group of the optically active dicarboxylic acid derivatives, the diamines and the diols comprise at least one aliphatic carbon chain with up to 15 carbon atoms and at least one terminal unsaturation.

4. The optically active adsorbent according to claim 2, wherein the hydroxy acid is a network polymerized tartaric acid derivative of the general formula:

(I)

$$R_1-C(=O)-C(H)(OR_2)-C(OR_2)(H)-C(=O)-R_1$$

wherein $R_1$ is a group RNH—, RO—, RR'N or HO— and $R_2$ is a group RNHCO—, RCO—, ROCO—, R— or H—, R being an aliphatic hydrocarbon residue having up to 15 carbon atoms, an aryl group, an aralkyl group, a naphthyl group or an anthryl group and R' being hydrogen or an alkyl group having up to 7 carbon atoms, the derivatives containing at least two groups $R_1$ or $R_2$ containing an aliphatic unsaturation, and the network polymerized tartaric acid derivatives being covalently bonded to the surface of a solid carrier material.

5. An adsorbent according to claim 4, wherein the tartaric acid derivatives have the general formula (Ia)

$$CH_2=CH-CH_2-N(H)-C(=O)-C(H)(OR_2)-C(OR_2)(H)-C(=O)-N(H)-CH_2-CH=CH_2$$

wherein $R_2$ is a group RNHCO—, RCO— or H and R is an aliphatic hydrocarbon residue having up to 15 carbon atoms, an aryl group, an aralkyl group, a naphthyl group or an anthryl group.

6. An adsorbent according to claim 5, wherein R is a substituted or unsubstituted aryl group, an aralkyl group, a naphthyl group or an anthryl group.

7. An adsorbent according to claim 6, wherein the tartaric acid derivatives have the general formula (Ib)

$$Ph-C(CH_3)(H)-N(H)-C(=O)-C(H)(OR_2)-C(OR_2)(H)-C(=O)-N(H)-C(CH_3)(H)-Ph$$

wherein $R_2$ is a group RNHCO— or RCO—, R being an aliphatic hydrocarbon residue having up to 15 carbon atoms and containing an aliphatic double bond.

8. An adsorbent according to claim 7, wherein $R_2$ is the group $$CH_2=C(CH_3)-C(=O)- \text{ or } CH_2=CH-CH_2-N(H)-C(=O)-$$

9. An adsorbent according to claim 1, wherein the solid carrier material is silica.

10. A method for preparing an optically active adsorbent, wherein tartaric acid derivatives as defined in claim 4 are network polymerized by radical polymerization or through hydrosilylation in the presence of solid carrier material.

11. A method according to claim 10, wherein the derivatives are polymerized through hydrosilylation in the presence of hydrosilanes or hydrosiloxanes of the general formula $$R-Si(R)(R)-X-[Si(Y)(Y)-X]_n-Si(R)(R)-R$$

wherein ⁻R is an alkyl group having from 1 to 4 carbon atoms or H or a mixture thereof,
X is $(CH_2)_m$ or O, and Y is R or the group —O—Si(R)$_3$, and n is an integer from 0 to 3000,
m is an integer from 1 to 10.

12. An optically active adsorbent obtainable by radical polymerization or polymerization through hydrosilylation of tartaric acid derivatives as defined in claim 4 in the presence of a solid carrier material.

13. An optically active adsorbent according to claim 12, obtainable by hydrosilylation polymerization.

14. A method for preparing an optically active adsorbent, wherein tartaric acid derivatives as defined in claim 4 are network polymerized through hydrosilylation in the presence of a hydrosilane or hydrosiloxan of the general formula $$R-Si(R)(R)-X-[Si(Y)(Y)-X]_n-Si(R)(R)-R$$

wherein R is an alkyl group having from 1 to 4 carbon atoms or H or a mixture thereof,
X is $(CH_2)_m$ or O, and Y is R or the group —O—Si(R)$_3$, and n is an integer from 0 to 3000,
m is an integer from 1 to 10, and the resulting network polymer is thereafter anchored to the surface of solid carrier material in the presence of a catalyst and at polymerization temperature.

15. An optically active adsorbent made according to claim 14, wherein the tartaric acid derivative has the general formula

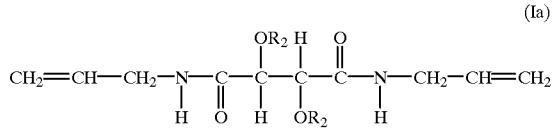 (Ia)

wherein $R_2$ is a group RNHCO—, RCO— or H and R is an aliphatic hydrocarbon residue having up to 15 carbon atoms, an aryl group, an aralkyl group, a naphthyl group or an anthryl group.

16. An optically active adsorbent made according to claim 14, wherein the tartaric acid derivative has the general formula

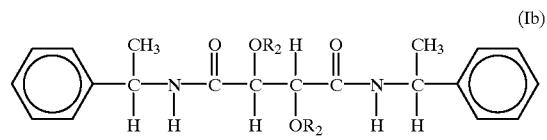 (Ib)

wherein $R_2$ is a group RNCO— or RCO—, R being an aliphatic hydrocarbon residue having up to 15 carbon atoms containing an aliphatic double bond.

17. An optically active adsorbent obtaining by network polymerization through hydrosilylation of a tartaric acid derivative as defined in claim 4 in the presence of a hydrosilane or a hydrosiloxane of the general formula

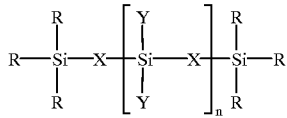

wherein R is an alkyl group having from 1 to 4 carbon atoms or H or a mixture thereof, X is $(CH_2)_m$ or O, and Y is R or the group —O—Si(R)$_3$, and n is an integer from 0 to 3000, m is an integer from 1 to 10, followed by anchoring the obtained network polymer to the surface of a solid carrier material in the presence of a catalyst and at polymerization temperature.

18. A network polymer obtainable by polymerization through hydrosilylation of a tartaric acid derivative as defined in claim 4 in the presence of a hydrosilane or hydrosiloxane having the general formula

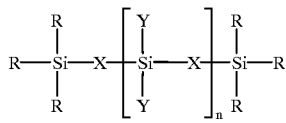

wherein R is an alkyl group having from 1 to 4 carbon atoms or H or a mixture thereof, X is $(CH_2)_m$ or O, and Y is R or the group —O—Si(R)$_3$, and n is an integer from 0 to 3000, m is an integer from 1 to 10.

19. A method for chromatographic separation of racemic mixtures in enantiomers, wherein said racemic mixture is chromatographed on an optically active adsorbent as defined in claim 1.

20. The optically active adsorbent according to claim 2, wherein said optically active network polymer comprises optically active derivatives of compounds selected from the group consisting of D- or L- tartaric acid, (1R, 2R)-(−)-1,2 diamino cyclohexan, (+)-2,2'-diamino binaphthyl-(1,1'), (1R,2R)-(−)-1,2-cyclohexan diol, (+)-(2R,3R)-1,4-dimethoxy-2,3-butandiol, D-(−)-citramalic acid and D-(+)-malic acid.

* * * * *